United States Patent [19]

Kulprathipanja

[11] Patent Number: 4,720,579
[45] Date of Patent: Jan. 19, 1988

[54] SEPARATION OF CITRIC ACID FROM FERMENTATION BROTH WITH A NEUTRAL POLYMERIC ADSORBENT

[75] Inventor: Santi Kulprathipanja, Hoffman Estates, Ill.

[73] Assignee: UOP Inc., Des Plaines, Ill.

[21] Appl. No.: 943,219

[22] Filed: Dec. 18, 1986

[51] Int. Cl.⁴ ............................................. C07C 51/42
[52] U.S. Cl. ..................................... 562/580; 562/584
[58] Field of Search ................................. 562/580, 584

[56] References Cited

U.S. PATENT DOCUMENTS

| | | | |
|---|---|---|---|
| 3,531,463 | 9/1970 | Gustafson | 260/211.5 |
| 3,663,467 | 5/1972 | Albright | 260/2.5 B |
| 3,904,684 | 9/1975 | Tsuda et al. | 562/580 |

FOREIGN PATENT DOCUMENTS

| | | | |
|---|---|---|---|
| 688245 | 6/1964 | Canada | 562/580 |
| 2931759 | 2/1981 | Fed. Rep. of Germany | 562/580 |
| 3506944 | 10/1985 | Fed. Rep. of Germany | 562/580 |

OTHER PUBLICATIONS

Johnson, J. Sci. Food Agric., vol. 33 (3), pp. 287–293.
Handbook of Chemistry & Physics, 53rd Edition, 1972–1973, CRC Press.

*Primary Examiner*—Paul J. Killos
*Attorney, Agent, or Firm*—Thomas K. McBride; John F. Spears, Jr.; Jack H. Hall

[57] ABSTRACT

Citric acid is separated from a fermentation broth by using an adsorbent comprising a neutral, noniogenic, macroreticular, water-insoluble, crosslinked styrene-poly(vinyl)benzene and a desorbent comprising water and, optionally, acetone with the water. The pH of the feed is adjusted and maintained below the first ionization constant ($pKa_1$) of citric acid to maintain selectivity.

23 Claims, 21 Drawing Figures

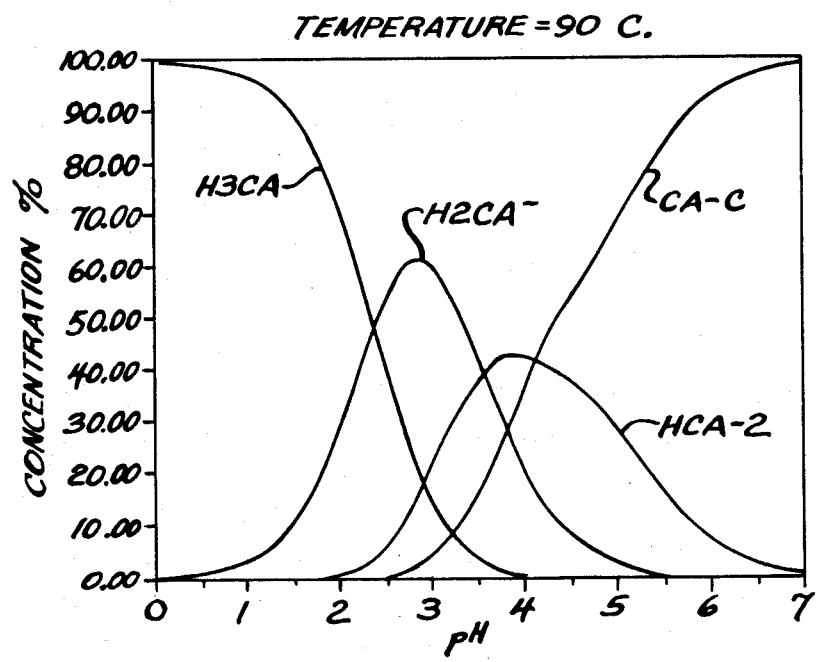
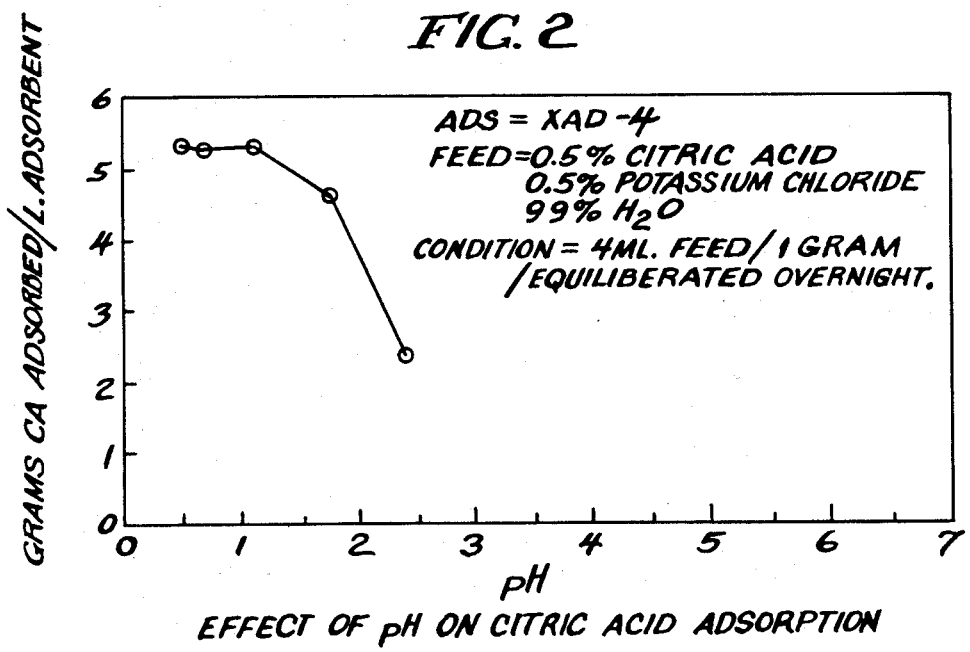

SEPARATION OF CITRIC ACID FROM FERMENTATION BROTH WITH A NEUTRAL POLYMERIC ADSORBENT

FIELD OF THE INVENTION

The field of art to which this invention pertains is the solid bed adsorptive separation of citric acid from fermentation broths containing citric acid, carbohydrates, amino acids, proteins and salts. More specifically, the invention relates to a process for separating citric acid which process employs an adsorbent comprising particular polymers which selectively adsorb citric acid from a fermentation mixture containing citric acid.

BACKGROUND OF THE INVENTION

Citric acid is used as a food acidulant, and in pharmaceutical, industrial and detergent formulations. The increased popularity of liquid detergents formulated with citric acid has been primarily responsible for growth of worldwide production of citric acid to about 700 million pounds per year which is expected to continue in the future.

Citric acid is produced by a submerged culture fermentation process which employs molasses as feed and the microorganism, Aspergillus Niger. The fermentation product will contain carbohydrates, amino acids, proteins and salts as well as citric acid, which must be separated from the fermentation broth.

There are two technologies currently employed for the separation of citric acid. The first involves calcium salt precipitation of citric acid. The resulting calcium citrate is acidified with sulfuric acid. In the second process, citric acid is extracted from the fermentation broth with a mixture of trilaurylamine, n-octanol and a $C_{10}$ or $C_{11}$ isoparaffin. Citric acid is reextracted from the solvent phase into water with the addition of heat. Both techniques, however, are complex, expensive and they generate a substantial amount of waste for disposal.

The patent literature has suggested a possible third method for separating citric acid from the fermentation broth, which involves membrane filtration to remove raw materials or high molecular weight impurities and then adsorption of contaminants onto a nonionic resin based on polystyrene or polyacrylic resins and collection of the citric acid in the rejected phase or raffinate and crystallization of the citric acid after concentrating the solution, or by precipitating the citric acid as the calcium salts then acidifying with $H_2SO_4$, separating the $CaSO_4$ and contacting cation- and anion-exchangers. This method, disclosed in European Published Application No. 151,470, Aug. 14, 1985, is also a rather complex and lengthy method for separating the citric acid. In contrast, my method makes it possible to separate the citric acid in a single step and to adsorb the citric acid by the adsorbent and obtain the purified citric acid in the desorbent.

SUMMARY OF THE INVENTION

This invention relates to a process for adsorbing citric acid from a fermentation broth onto a neutral polymeric adsorbent such as nonionogenic, macroreticular, water-insoluble, crosslinked styrenepoly(vinyl)benzene copolymers and copolymers thereof with polymerizable ethylenically unsaturated monomers other than poly(-vinyl)benzenes and recovering the citric acid by desorption thereof with a desorbent under desorption conditions. One aspect of the invention is in the discovery that complete separation of citric acid from salts and carbohydrates is only achieved by adjusting and maintaining the pH of the feed solution lower than the first ionization constant ($pKa_1$) of citric acid (3.13). The degree to which the pH must be lowered to maintain adequate selectivity appears to be interdependent on the concentration of citric acid in the feed mixture; the pH is inversely dependent on the concentration. As concentrations are decreased below 13% to very low concentrations, the pH may be near the $pKa_1$ of citric acid of 3.13; at 13%, the pH may range from 0.9 to 1.7; however, at 40% citric acid feed concentration, the pH must be lowered to at least about 1.2 or lower. At higher concentrations, the pH must be even lower; for example, at 50% citric acid, the pH must be at or below 1.0. Another aspect of the invention is the discovery that the temperature of separation can be reduced by the addition of acetone, or other low molecular weight ketone, to the desorbent; the higher temperatures associated with adsorbent breakdown can thus be avoided.

Other aspects of the invention encompass details of feed mixtures, adsorbents, desorbents and operating conditions which are hereinafter disclosed.

BRIEF DESCRIPTION OF THE DRAWINGS

FIG. 1 is a plot of concentration of various citric acid species versus the pH of citric acid dissociation which shows the shifting of the equilibrium point of the citric acid dissociation by varying the concentration of citric acid, citrate anions and the hydrogen ion.

FIG. 2 is a static plot to determine the effect of pH on amount of citric acid that can be adsorbed by the adsorbent.

DESCRIPTION OF THE INVENTION

Figure 3A:
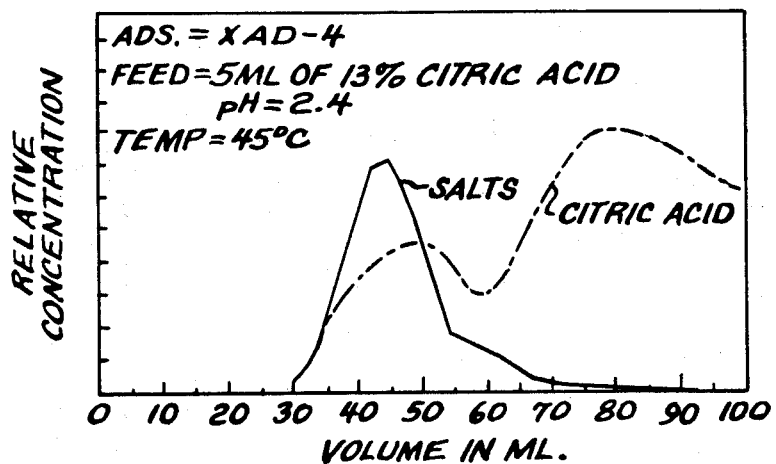
FIGS. 3A–C are the plots of the pulse tests in Example I using XAD-4 to separate citric acid from a feed containing 13% citric acid at pHs of 2.4, 1.7 and 0.9, respectively.

At the outset the definitions of various terms used throughout the specification will be useful in making clear the operation, objects and advantages of my process.

A "feed mixture" is a mixture containing one or more extract components and one or more raffinate components to be separated by my process. The term "feed stream" indicates a stream of a feed mixture which passes to the adsorbent used in the process.

An "extract component" is a compound or type of compound that is more selectively adsorbed by the adsorbent while a "raffinate component" is a compound or type of compound that is less selectively adsorbed. In this process, citric acid is an extract component and salts and carbohydrates are raffinate components. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream and preferably at least a portion of the raffinate stream from the separation process are passed to separation means, typically fractionators, where at least a portion of desorbent material is separated to produce an extract product and a raffinate product. The terms "extract product" and "raffinate product" mean products produced by the process containing, respectively, an extract component and a raffinate component in higher concentrations than those found in the extract stream and the raffinate stream. Although it is possible by the process of this invention to produce a high purity, citric acid product at high recoveries, it will be appreciated that an extract component is never completely adsorbed by the adsorbent. Likewise, a raffinate component is completely nonadsorbed by the adsorbent. Therefore, varying amounts of a raffinate component can appear in the extract stream and, likewise, varying amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of citric acid to that of the less selectively adsorbed components will be lowest in the raffinate stream, next highest in the feed mixture, and the highest in the extract stream. Likewise, the ratio of the concentration of the less selectively adsorbed components to that of the more selectively adsorbed citric acid will be highest in the raffinate stream, next highest in the feed mixture, and the lowest in the extract stream.

The term "selective pore volume" of the adsorbent is defined as the volume of the adsorbent which selectively adsorbs an extract component from the feed mixture. The term "nonselective void volume" of the adsorbent is the volume of the adsorbent which does not selectively retain an extract component from the feed mixture. This volume includes the cavities of the adsorbent which contain no adsorptive sites and the interstitial void spaces between adsorbent particles. The selective pore volume and the nonselective void volume are generally expressed in volumetric quantities and are of importance in determining the proper flow rates of fluid required to be passed into an operational zone for efficient operations to take place for a given quantity of adsorbent. When adsorbent "passes" into an operational zone (hereinafter defined and described) employed in one embodiment of this process its nonselective void volume together with its selective pore volume carries fluid into that zone. The nonselective void volume is utilized in determining the amount of fluid which should pass into the same zone in a countercurrent direction to the adsorbent to displace the fluid present in the nonselective void volume. If the fluid flow rate passing into a zone is smaller than the nonselective void volume rate of adsorbent material passing into that zone, there is a net entrainment of liquid into the zone by the adsorbent. Since this net entrainment is a fluid present in nonselective void volume of the adsorbent, it in most instances comprises less selectively retained feed components. The selective pore volume of an adsorbent can in certain instances adsorb portions of raffinate material from the fluid surrounding the adsorbent since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

The feed material contemplated in this invention is the fermentation product obtained from the submerged culture fermentation of molasses by the microorganism, Aspergillus Niger. The fermentation product will have a composition exemplified by the following:

| Citric acid | 12.9% ± 3% |
| --- | --- |
| Salts | 6,000 ppm |
| Carbohydrates (sugars) | 1% |
| Others (proteins and amino acids) | 5% |

The salts will be K, Na, Ca, Mg and Fe. The carbohydrates are sugars including glucose, xylose, mannose, oligosaccharides of DP2 and DP3 plus as many as 12 or more unidentified saccharides. The composition of the feedstock may vary from that given above and still be used in the invention. However, juices such as citrus fruit juices, are not acceptable or contemplated because other materials contained therein will be adsorbed at the same time rather than citric acid alone.

Johson, *J. Sci. Food Agric.*, Vol 33 (3) pp 287-93.

I have discovered that the separation of citric acid can be enhanced significantly by adjusting the pH of the feed to a level below the first ionization constant of citric acid. The first ionization constant ($pKa_1$) of citric acid is 3.13, *Handbook of Chemistry & Physics*, 53rd Edition, 1972-3, CRC Press, and therefore, the pH of the citric acid feed should be below 3.13. When the pH for a 13% concentrated solution of citric acid is 2.4 or greater, for example, as in FIG. 3A (Example I), citric acid "breaks through" (is desorbed) with the salts and carbohydrates at the beginning of the cycle, indicating that all the citric acid is not adsorbed. In contrast, less "break through" of citric acid is observed when the pH is 1.7 and no "break through" when the pH is 0.9 at the 13% level, for example as in Examples 3B and 3C, respectively. I cannot state the reasons for this effect, but, without being bound by my theory, I believe that the following explanation may be correct:

The polymeric adsorbents of the invention are nonionic and hydrophobic and, therefore, will selectively adsorb nonionic species compared to ionic species. Thus, I have applied this knowledge to the separation of the nonionic citric acid species from the ionic species.

In aqueous solution, unionized citric acid exists in equilibrium with the several citrate anions and hydrogen ions. This is shown in the following equations, where the acid dissociation constants, pKa$_1$, pKa$_2$ and pKa$_3$ of citric acid at 25° C. are 3.13, 4.74 and 5.40, respectively:

the feed mixture that is passed into the process. Both the raffinate stream and the extract stream are removed from the adsorbent in admixture with desorbent material and without a method of separating at least a por-

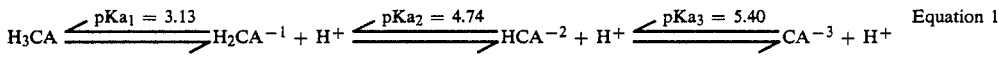

Equation 1

The equilibrium point of citric acid dissociation can be shifted by varying the concentrations of citric acid, the citrate anion or the hydrogen ion. This is demonstrated in FIG. 1, for the concentration of the several citric acid species in solution versus pH at 90° C. The result shows a higher percent of nonionized citric acid (H$_3$CA) at a higher hydrogen ion concentration (lower pH). Decreasing the pH (raising the H$^+$ ion concentration) will introduce more nonionized citric acid while reducing the citrate anionic species (H$_2$CA$^{-1}$, HCA$^{-2}$ and CA$^{-3}$) in the solution.

Based on the citric acid equilibrium and the resin properties mentioned above, nonionized citric acid will be separated from other ionic species (including citrate anions) in the fermentation broths using the resin adsorbents described. However, for a higher citric acid recovery, a lower pH solution is required. The static adsorption isotherm of a particular resin falling within the invention, Amberlite XAD-4, for citric acid was carried out at room temperature about 25° C., as a function of feed pH. FIG. 2 shows the results of the study. The results show adsorption of the nonionic citric acid as the pH is lowered. This agrees well with my concept mentioned earlier that XAD-4 will selectively adsorb the nonionic species compared to the ionic ones, and that nonionized citric acid is the predominant species at lower pH. Further verification will be presented in the Examples given hereinafter.

Desorbent materials used in various prior art adsorptive separation processes vary depending upon such factors as the type of operation employed. In the swing bed system, in which the selectively adsorbed feed component is removed from the adsorbent by a purge stream, desorbent selection is not as critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Desorbent materials should additionally be substances which are easily separable from tion of the desorbent material the purity of the extract product and the raffinate product would not be very high, nor would the desorbent material be available for reuse in the process. It is therefore contemplated that any desorbent material used in this process will preferably have a substantially different average boiling point than that of the feed mixture to allow separation of at least a portion of the desorbent material from feed components in the extract and raffinate streams by simple fractional distillation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture. Finally, desorbent materials should also be materials which are readily available and therefore reasonable in cost. In the preferred isothermal, isobaric, liquid phase operation of the process of my invention, I have found water a particularly effective desorbent material. Also, for certain reasons, I have found acetone and other low molecular weight ketones, such as methylethyl ketone and diethyl ketone to be effective in admixture with water in small amounts, up to 15%. The key to their usefulness lies in their solubility in water. Their advantage, however, lies in their ability to reduce the temperature at which the desorption can take place. With some adsorbates and water as desorbent, the temperature must be raised to aid the desorption step. Increased temperatures can cause premature deactivation of the adsorbent. A solution to that problem in this particular separation is to add acetone in the amount of 1% to 15% of the desorbent, preferably, 1% to 10% with the most preferred range of 5–10%. The low molecular weight ketone may also affect the adsorbent stability in possibly two ways, by removing solubilizing components which cause deactivation or by effecting regeneration, i.e., by removing the deactivating agent or reversing its effect. I have demonstrated the reduction of the desorption temperature of this separation by approximately 50° C. by adding 10% acetone to the desorbent. A reduction of from about 5° C. to about 70° C. can be achieved by the addition of 1% to 15% acetone to the water desorbent.

The prior art has also recognized that certain characteristics of adsorbents are highly desirable, if not absolutely necessary, to the successful operation of a selective adsorption process. Such characteristics are equally important to this process. Among such characteristics are: (1) adsorptive capacity for some volume of an extract component per volume of adsorbent; (2) the selective adsorption of an extract component with respect to a raffinate component and the desorbent material; and (3) sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions. Relative selectivity is shown as Equation 1 below:

$$\text{Selectivity} = (B) = \frac{[\text{vol. percent } C/\text{vol. percent } D]_A}{[\text{vol. percent } C/\text{vol. percent } D]_U} \quad \text{Equation 1}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases. Where selectivity of two components approaches 1.0 there is no preferential adsorption of one component by the adsorbent with respect to the other; they are both adsorbed (or nonadsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greater than 1, it is preferred that such selectivity approach a value of 2. Like relative volatility, the higher the selectivity, the easier the separation is to perform. Higher selectivities permit a smaller amount of adsorbent to be used. The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

Resolution is a measure of the degree of separation of a two-component system, and can assist in quantifying the effectiveness of a particular combination of adsorbent, desorbent, conditions, etc. for a particular separation. Resolution for purposes of this application is defined as the distance between the two peak centers divided by the average width of the peaks at $\frac{1}{2}$ the peak height as determined by the pulse tests described hereinafter. The equation for calculating resolution is thus:

$$R = \frac{L_2 - L_1}{\frac{1}{2}(W_1 + W_2)} \quad \text{Equation 2}$$

where $L_1$ and $L_2$ are the distance, in ml, respectively, from a reference point, e.g., zero to the centers of the peaks and $W_1$ and $W_2$ are the widths of the peaks at $\frac{1}{2}$ the height of the peaks.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber comprising a helical column of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent, is injected for a duration of several minutes. Desorbent flow is resumed, and the tracer and the extract component or the raffinate component (or both) are eluted as in a liquid-solid chromatographic operation. The effluent can be analyzed onstream or, alternatively, effluent samples can be collected periodically and later analyzed separately by analytical equipment and traces of the envelopes of corresponding component peaks developed.

From information derived from the test adsorbent, performance can be in terms of void volume, retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is again the volume of desorbent pumped during this time interval.

To further evaluate promising adsorbent systems and to translate this type of data into a practical separation process requires actual testing of the best system in a continuous countercurrent liquid-solid contacting device. The general operating principles of such a device have been previously described and are found in Broughton U.S. Pat. No. 2,985,589. A specific laboratory size apparatus utilizing these principles is described in deRosset et al., U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and the raffinate and extract streams are being withdrawn through two more. All remaining access lines are inactive and when the position of the distributing valve is advanced by one index, all active positions will be advanced by one bed. This simulates a condition in which the adsorbent physically moves in a direction countercurrent to the liquid flow. Additional details on the abovementioned nonionic adsorbent testing apparatus and adsorbent evaluation techniques may be found in the paper "Separation of C$_8$ Aromatics by Adsorption" by A. J. deRosset, R. W. Neuzil, D. J. Korous, and D. H. Rosback presented at the American Chemical Society, Los Angeles, Calif., Mar. 28 through Apr. 2, 1971.

Adsorbents to be used in the process of this invention will comprise nonionogenic, hydrophobic, water-insoluble, crosslinked styrene-poly(vinyl)benzene copolymers and copolymers thereof with monoethylenically unsaturated compounds or polyethylenically unsaturated monomers other than poly(vinyl)benzenes, including the acrylic esters, such as those described in Gustafson U.S. Pat. Nos. 3,531,463 and 3,663,467, both incorporated herein by reference, although not limited thereto. As stated in U.S. Pat. No. 3,531,463, the polymers may be made by techniques disclosed in U.S. Ser. No. 749,526, filed July 18, 1958, now U.S. Pat. Nos. 4,221,871; 4,224,415; 4,256,840; 4,297,220; 4,382,124 and 4,501,826 to Meitzner et al., all of which are incorporated herein by reference. Adsorbents such as just described are manufactured by the Rohm and Haas Company, and sold under the trade name "Amberlite." The types of Amberlite polymers known to be effective for use by this invention are referred to in Rohm and Haas Company literature as Amberlite adsorbents XAD-1, XAD-2, XAD-4, XAD-7 and XAD-8, and described in the literature as "hard, insoluble spheres of high surface, porous polymer." The various types of Amberlite polymeric adsorbents differ somewhat in physical properties such as porosity volume percent, skeletal density and nominal mesh sizes, but more so in surface area, average pore diameter and dipole moment. The preferred adsorbents will have a surface area of 10–2000 square meters per gram and preferably from 100–1000 m$^2$/g. These properties are listed in the following table:

TABLE 1

| Chemical Nature | XAD-1 Polystyrene | XAD-2 Polystyrene | XAD-4 Polystyrene | XAD-7 Acrylic Ester | XAD-8 Acrylic Ester |
|---|---|---|---|---|---|
| Porosity Volume % | 37 | 42 | 51 | 55 | 52 |
| True Wet Density grams/cc | 1.02 | 1.02 | 1.02 | 1.05 | 1.09 |
| Surface Area M$^2$/gram | 100 | 300 | 780 | 450 | 160 |
| Average Pore Diameter Angstroms | 200 | 90 | 50 | 90 | 225 |
| Skeletal Density grams/cc | 1.07 | 1.07 | 1.08 | 1.24 | 1.23 |
| Nominal Mesh Size | 20–50 | 20–50 | 20–50 | 20–50 | 25–50 |
| Dipole Moment of Functional Groups | 0.3 | 0.3 | 0.3 | 1.8 | 1.8 |

Applications for Amberlite polymeric adsorbents suggested in the Rohm and Haas Company literature include decolorizing pulp mill bleaching effluent, decolorizing dye wastes and removing pesticides from waste effluent. There is, of course, no hint in the literature of my surprising discovery of the effectiveness of Amberlite polymeric adsorbents in the separation of citric acid from Aspergillus-Niger fermentation broths.

The adsorbent may be employed in the form of a dense compact fixed bed which is alternatively contacted with the feed mixture and desorbent materials. In the simplest embodiment of the invention the adsorbent is employed in the form of a single static bed in which case the process is only semicontinuous. In another embodiment a set of two or more static beds may be employed in fixed bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Countercurrent moving bed or simulated moving bed countercurrent flow systems, however, have a much greater separation efficiency than fixed adsorbent bed systems and are therefore preferred. In the moving bed or simulated moving bed processes the adsorption and desorption operations are continuously taking place which allows both continuous production of an extract and a raffinate stream and the continual use of feed and desorbent streams. One preferred embodiment of this process utilizes what is known in the art as the simulated moving bed countercurrent flow system. The operating principles and sequence of such a flow system are described in U.S. Pat. No. 2,985,589 incorporated herein by reference thereto. In such a system it is the progressive movement of multiple liquid access points down an adsorbent chamber that simulates the upward movement of adsorbent contained in the chamber. Only four of the access lines are active at any one time; the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divided the adsorbent chamber into separate zones, each of which has a different function. In this embodiment of my process it is generally necessary that three separate operational zones be present in order for the process to take place although in some instances an optional fourth zone may be used.

The adsorption zone, zone 1, is defined as the adsorbent located between the feed inlet stream and the raffinate outlet stream. In this zone, the feedstock contacts the adsorbent, extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the nonselective void volume of the adsorbent of any raffinate material carried into zone 2 by shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances one of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

It is contemplated that at least a portion of the extract output stream will pass into a separation means wherein at least a portion of the desorbent material can be separated to produce an extract product containing a reduced concentration of desorbent material. Preferably, but not necessary to the operation of the process, at least a portion of the raffinate output stream will also be passed to a separation means wherein at least a portion of the desorbent material can be separated to produce a desorbent stream which can be reused in the process and a raffinate product containing a reduced concentration of desorbent material. The separation means will typically be a fractionation column, the design and operation of which is well-known to the separation art.

Reference can be made to D. B. Broughton U.S. Pat. No. 2,985,589, and to a paper entitled "Continuous Adsorptive Processing—A New Separation Technique" by D. B. Broughton presented at the 34th Annual Meeting of the Society of Chemical Engineers at Tokyo, Japan on Apr. 2, 1969, both incorporated herein by reference, for further explanation of the simulated moving bed countercurrent process flow scheme.

Although both liquid and vapor phase operations can be used in many adsorptive separation processes, liquid-phase operation is preferred for this purpose because of the lower temperature requirements and because of the higher yields of extract product than can be obtained with liquid-phase operation over those obtained with vapor-phase operation. Absorption conditions will include a temperature range of from about 20° C. to about 200° C. with about 65° C. to about 100° C. being more preferred and a pressure range of from about atmospheric to about 500 psig (3450 kPa gauge) being more preferred to ensure liquid phase. Desorption conditions will include the same range of temperatures and pressures as used for adsorption conditions.

The size of the units which can utilize the process of this invention can vary anywhere from those of pilot plant scale (see for example our assignee's U.S. Pat. No. 3,706,812, incorporated herein by reference) to those of commerical scale and can range in flow rates from as little as a few cc an hour up to many thousands of gallons per hour.

The following examples are presented to illustrate the selectivity relationship that makes the process of my invention possible. The example is not intended to unduly restrict the scope and spirit of claims attached hereto.

EXAMPLE I

In this example, three pulse tests were run with a neutral styrene divinylbenzene polymeric adsorbent (XAD-4 made by Rohm & Haas Company) to determine the ability of the adsorbent to separate citric acid, at different pHs, from its fermentation mixture of carbohydrates (DP1, DP2, DP3, including glucose, xylose, arabinose and raffinose) and ions of salts, including $Na^+$, $K^+$, $Mg^{++}$, $Ca^{++}$, $Fe^{+++}$, $Cl^-$, $SO_4^=$, $PO_4^\equiv$ and $NO_3^-$, amino acids and proteins. The first test was run at a pH of 2.4 and 45° C. Two further tests were run at a pH of 1.7 and 0.9. Citric acid was desorbed with water. The fermentation feed mixture had the following composition:

| Feed Composition | Amount | |
|---|---|---|
| Citric Acid | 12.9% | |
| Salts ($K^+$, $Na^+$, $Ca^{++}$, $Mg^{++}$ $Fe^{+++}$) | 0.60% | (6000 ppm) |
| Carbohydrates (Sugars) | 1% | |
| Others ($SO_4^=$, $Cl^-$, $PO_4^\equiv$, $NO_3^-$, proteins and amino acids) | 5% | |
| Water | 81.5% | |

Retention volumes and resolution were obtained using the pulse test apparatus and procedure previously described. Specifically, the adsorbent was tested in a 70 cc straight column using the following sequence of operations for the pulse test. Desorbent material was continuously run upwardly through the column containing the adsorbent at a nominal liquid hourly space velocity (LHSV) of about 1.0. A void volume was determined by observing the volume of desorbent required to fill the packed dry column. At a convenient time the flow of desorbent material was stopped, and a 10 cc sample of feed mixture was injected into the column via a sample loop and the flow of desorbent material was resumed. Samples of the effluent were automatically collected in an automatic sample collector and later analyzed for salts and citric acid by chromatographic analysis. Some later samples were also analyzed for carbohydrates, but since they were eluted at approximately the same rate as the carbohydrates, they were not analyzed in these examples nor were other minor ingredients, amino acids and proteins. From the analysis of these samples, peak envelope concentrations were developed for the feed mixture components. The retention volume for the citric acid was calculated by measuring the distance from the midpoint of the net retention volume of the salt envelope as the reference point to the midpoint of the citric acid envelope. The resolution, R, is calculated from Equation 2, given earlier.

The results for these pulse tests are shown in the following table.

TABLE 2

| Component | Net retention Volume | Peak Width at 0.5 Height | Resolution (0.5 Height) |
|---|---|---|---|
| Test A - pH - 2.4 | | | |
| Salts | 0 | 14.4 | 1.39 |
| Citric acid | 44.4 | 49.5 | Reference |
| Test B - pH - 1.7 | | | |
| Salts | 0 | 11.6 | 1.49 |
| Citric acid | 42.2 | 45.1 | Reference |
| Test C - pH - 0.9 | | | |
| Salts | 0 | 13.3 | 1.4 |
| Citric acid | 40.9 | 45.1 | Reference |

Figure 3B:
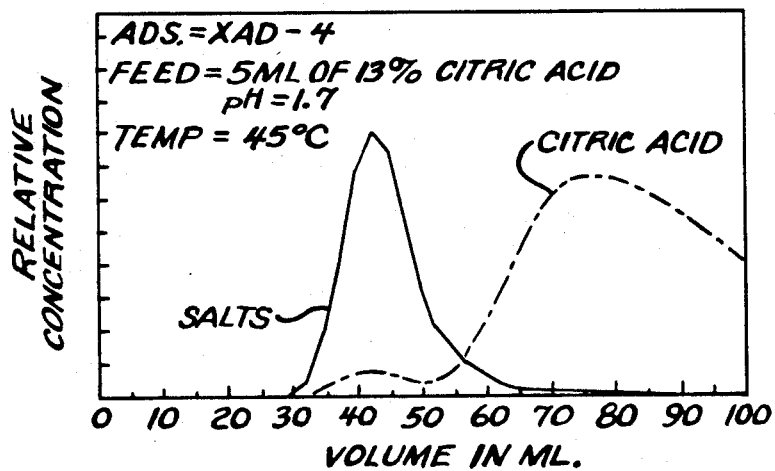
Figure 3C:
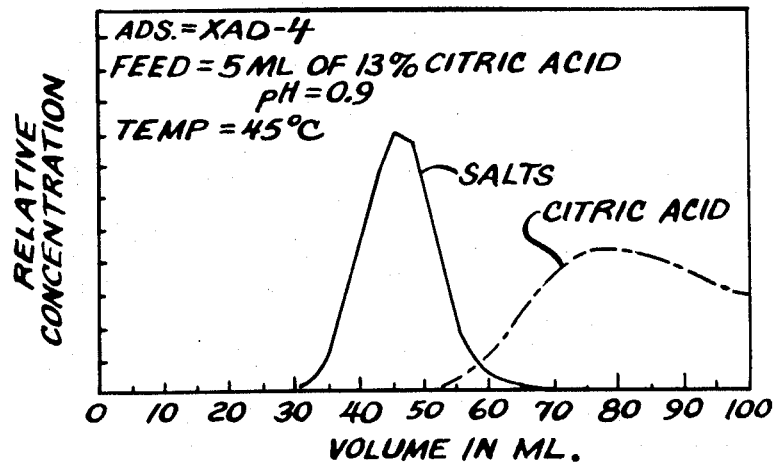

The results are also shown in FIG. 3A in which it is clear that while citric acid is more strongly adsorbed than the other components, there is a substantial loss of citric acid which is unadsorbed and removed with the salts and carbohydrates (not shown). Citric acid is satisfactorily separated in the process in FIG. 3B where the results are judged good and in FIG. 3C where the results were judged excellent. The process clearly will have commercial feasibility at a pH of 1.7 and lower. At a pH of 2.4 (FIG. 3A), however, it is noted that a substantial amount of the citric acid will be recovered, I theorize, as the citrate, $H_2CA^{-1}$, in the raffinate with the salts and carbohydrates. From this, I conclude that the ionized, soluble species should be reduced, as explained previously, by maintaining a lower pH in the feed, thereby driving the equilibrium in Equation 1 to the left.

EXAMPLE II

This example presents the results of using a neutral crosslinked styrene divinylbenzene (XAD-4) and a neutral crosslinked polyacrylic ester copolymer (XAD-8) with the same separation feed mixture as Example I at different pHs to demonstrate the poor separation when the pH is 2.4 or higher, or above the first ionization constant, $pKa_1=3.13$, of citric acid. The same procedure and apparatus previously described in Example I were used in the separation, except the temperature was 60° C. and 5 ml of feed mixture was used.

Figure 4A:
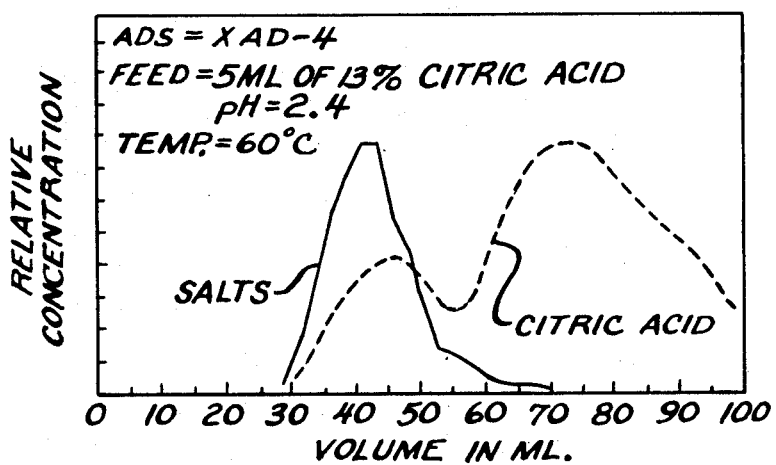
FIGS. 4A–E are plots of the pulse tests of Example II at pHs of 2.4, 1.7, 0.9, 2.8 and 1.4, respectively, run on different adsorbent samples.
Figure 4B:
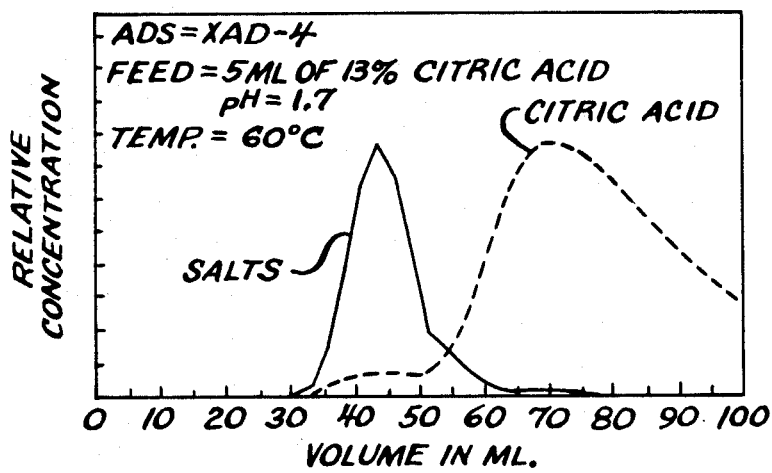
Figure 4C:
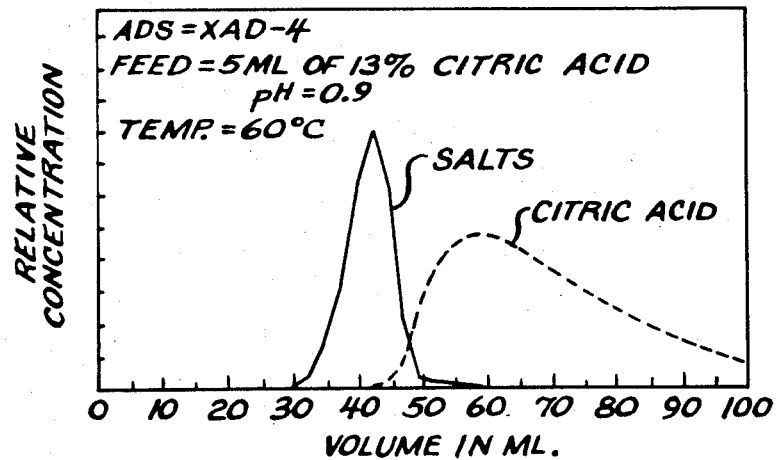

FIGS. 4A, 4B and 4C are, respectively, graphical presentations of the results of the pulse tests using XAD-4 at pHs, respectively, of 2.4, 1.7 and 0.9. FIG. 4A shows that citric acid "breaks through" with the salts (and carbohydrates). This problem can be partially alleviated by lowering the pH to 1.7 as in FIG. 4B. An excellent separation can be achieved by lowering the pH further to 0.9 as in FIG. 4C. This separation, with adjustments of the pH, again, clearly has commercial utility.

Figure 4D:
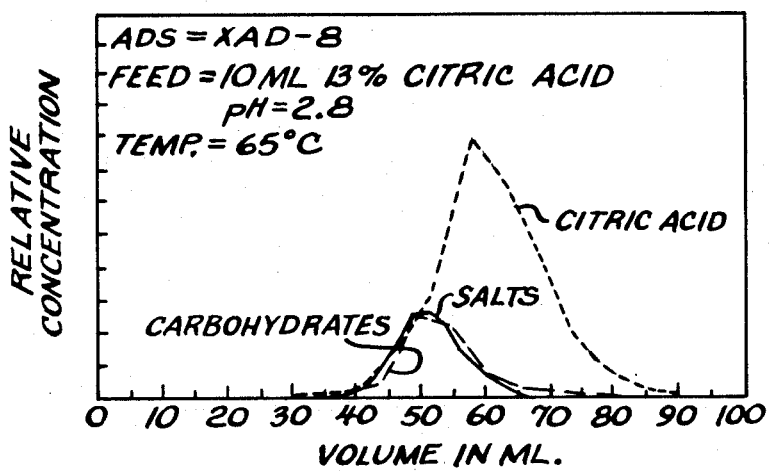
Figure 4E:
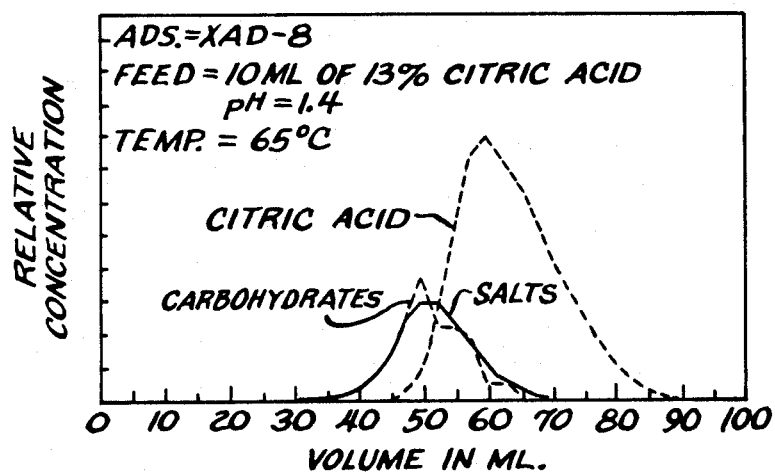

FIGS. 4D and 4E are, respectively, graphical representations of the results of pulse tests, run under the same conditions as above, using XAD-8 at pHs of 2.8 and 1.4 and temperatures of 65° C. FIG. 4D, which was made at a pH of 2.8, shows no separation, but rather the salts, carbohydrates and citric acid eluting together initially. After about 67 ml, after most of the carbohydrates and salts and some of the citric acid have been recovered, some relatively pure citric acid can be obtained, but recovery is low. FIG. 4E, which was made at a pH of 1.4, shows a selectivity between citric acid and carbohydrates and salts which results in a satisfactory separation and recovery of the citric acid.

EXAMPLE III

This example presents the results of using a neutral crosslinked styrene divinylbenzene copolymer (XAD-4) with the same separation feed mixture as Example I at two different pHs to demonstrate the poor separation when the pH is 2.4 or higher. The same procedure and apparatus previously described in Example I were used, except the temperature was 93° C. in FIGS. 5A and 5B and the amount of feed mixture was 10 ml.

Figure 5A:
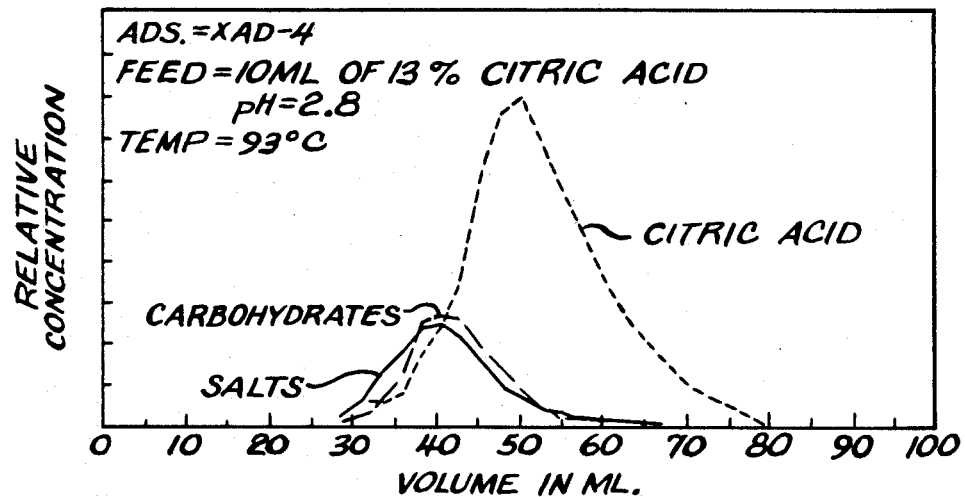
FIGS. 5A and B are plots of the pulse tests of Example III at pHs of 2.8 and 1.4, respectively, and temperatures of 93°.
Figure 5B:
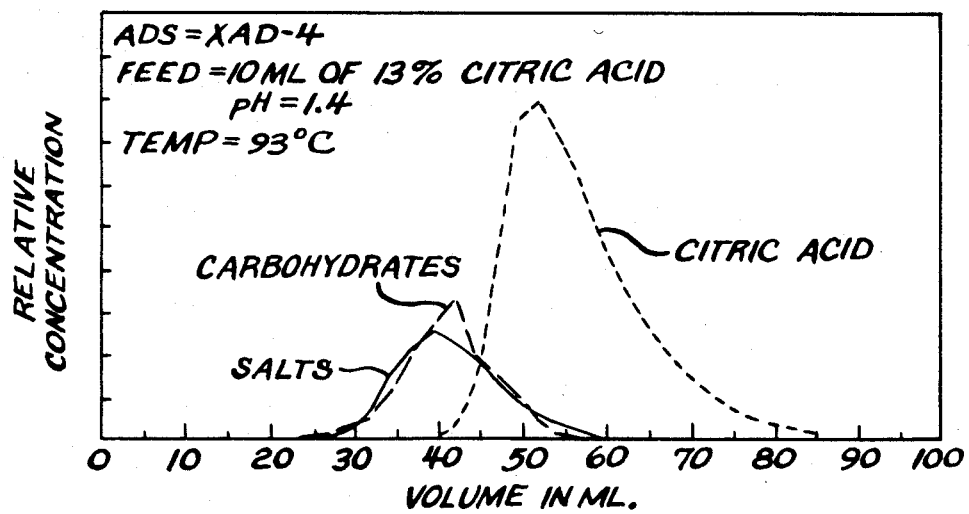

FIGS. 5A and 5B are, respectively, graphical presentations of the results of pulse tests using XAD-4 at pHs, respectively, of 2.8 and 1.4. FIG. 5A shows that citric acid "breaks through" with the salts and carbohydrates. This problem can be alleviated by lowering the pH to 1.4 as in FIG. 5B. This separation, with adjustment of the pH, again, clearly has commercial utility.

EXAMPLE IV

Figure 6A:
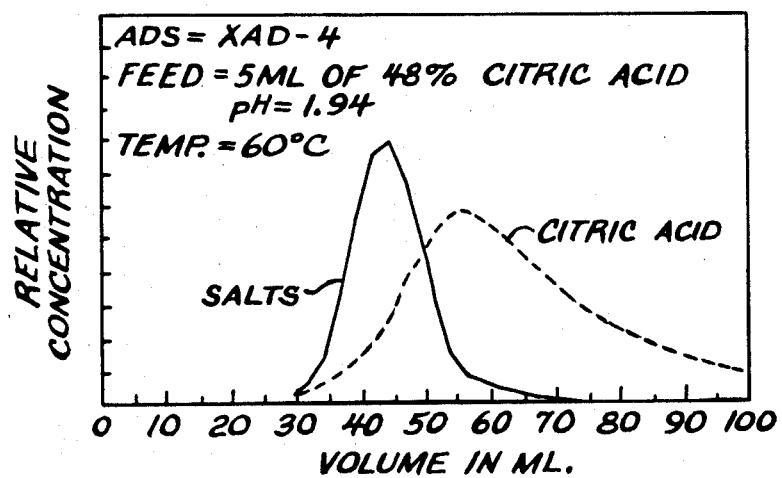
FIGS. 6A–C are plots of the pulse tests of Example IV at pHs of 1.94, 1.13 and 0.5, respectively.
Figure 6B:
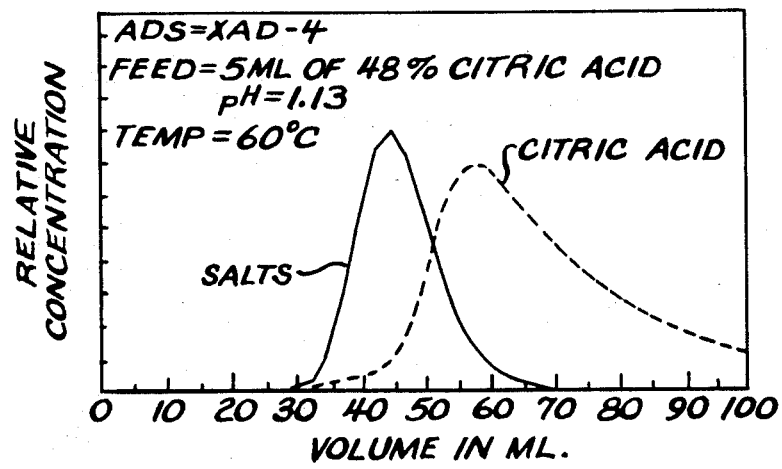
Figure 6C:
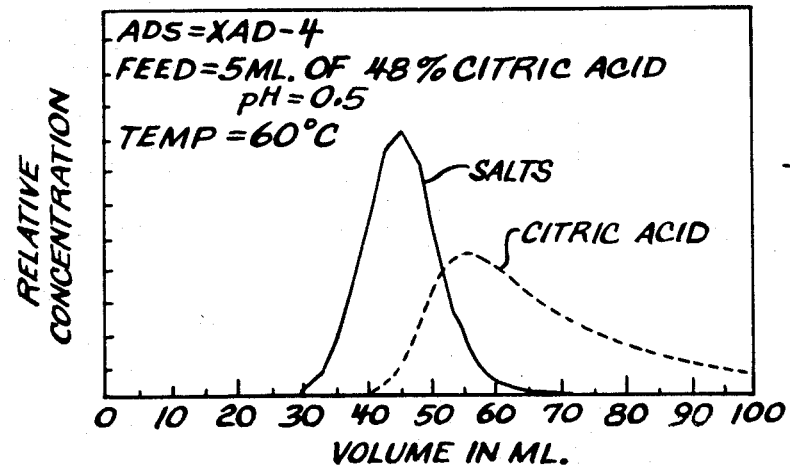

The procedure and apparatus previously described in Example I was used on the samples of this example. The temperature was 60° C. and 5 ml of feed mixture was used. The feed composition was similar to that previously used except that citric acid has been concentrated to 40% in the feed mixture. The effect of concentration on the pH will be seen. In FIG. 6A, even with the temperature at 60° C., the pH of 1.9 is too high to separate the citric acid at 40% concentration. By adjusting the pH downward as in FIGS. 6B and 6C, the citric acid is preferentially adsorbed and excellent separation is achieved at a pH of 0.5. In each of these samples, carbohydrates were not analyzed, but it can be assumed that the carbohydrates closely followed the salts in the separation.

EXAMPLE V

Figure 7A:
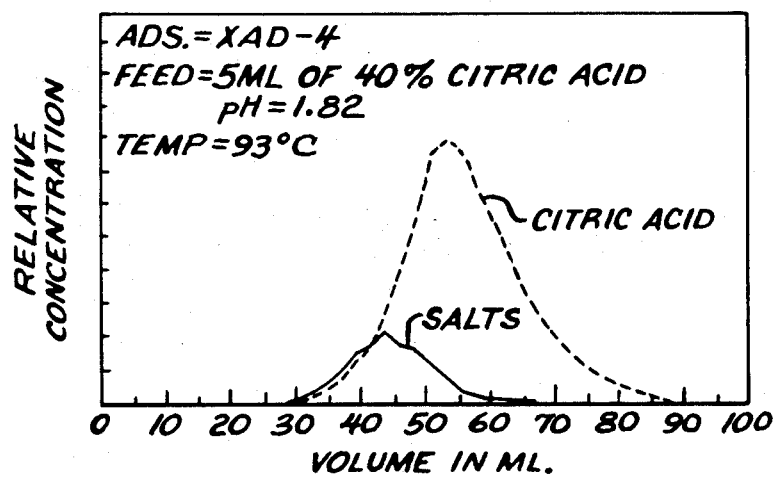
FIGS. 7A–C are plots of the pulse tests of Example V at pHs of 1.82, 0.5 and 0.3, respectively.

The procedure and apparatus previously described in Example I was used on the three samples of this example. The temperature was 93° C. and the amount of feed mixture was 5 ml. The feed composition was similar to that previously used except that citric acid has been concentrated to 40% in the feed mixture to demonstrate the further effect of concentration on the pH. In FIG. 7A, even with the temperature at 93° C., the pH of 1.8 is too high to separate the citric acid at 40% concentration. By adjusting the pH downward as in FIGS. 7B and 7C, the citric acid is preferentially adsorbed and excellent separation is achieved. Again, carbohydrates were not analyzed, but it can be assumed that the carbohydrates closely followed the salts in the separation.

EXAMPLE VI

Figure 8A:
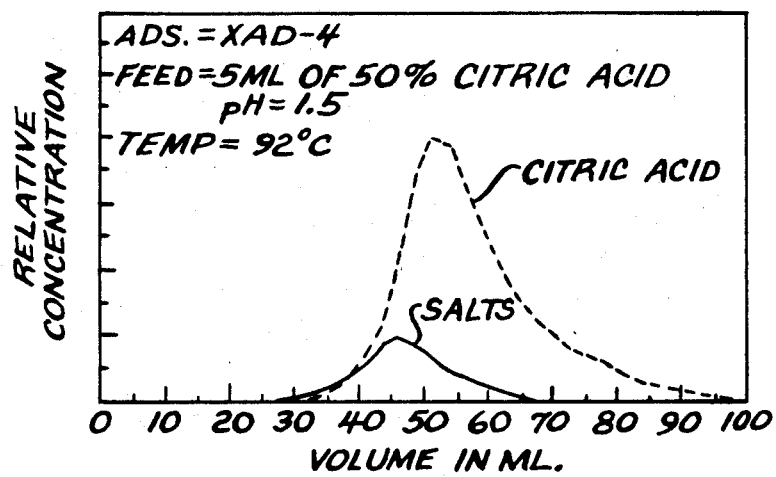
FIGS. 8A and B are plots of the pulse tests of Example VI at pHs of 1.5 and 1.0, respectively.
Figure 8B:
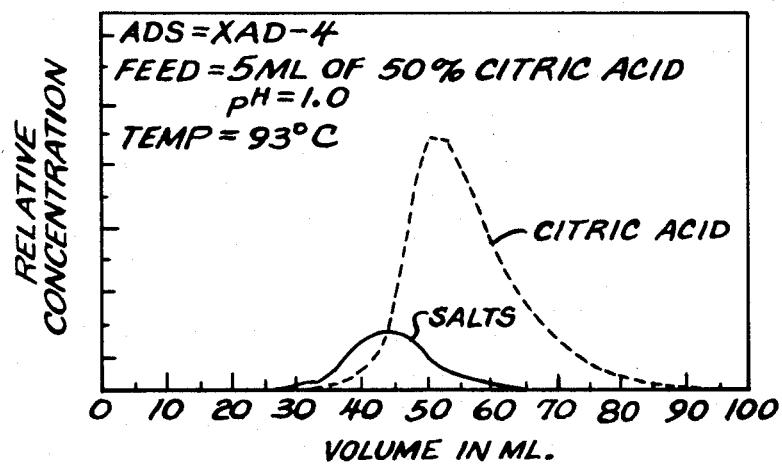

The pulse test of Example I was repeated on two 50% citric acid samples using XAD-4 adsorbent. The desorbent in both cases was water. The composition of the feed used was the same as used in Example I except that citric acid has been concentrated to 50%. The temperature was 93° C. In the first sample, the pH was 1.5. As shown in FIG. 8A, citric acid was not separated. After reducing the pH to 1.0 in the second sample, citric acid was readily separated as seen in FIG. 8B. Again, carbohydrates were not analyzed, but assumed to closely follow the salts. The separation in FIG. 8B was judged good.

EXAMPLE VII

Figure 9:
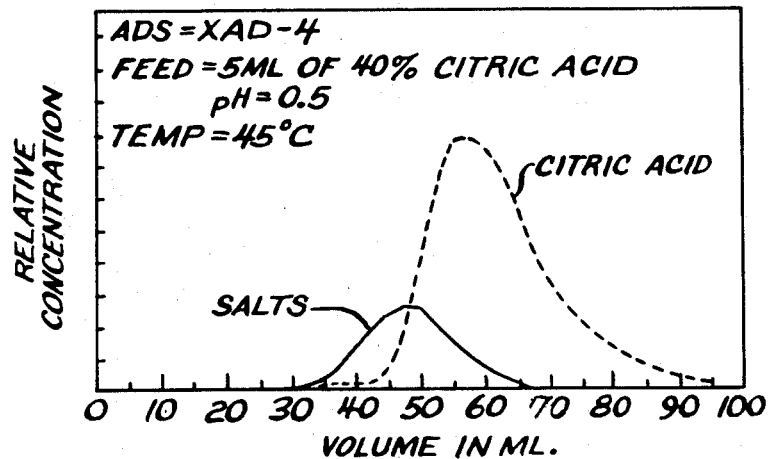
FIG. 9 is a plot of the pulse test in Example VII showing the adsorption achieved at lower temperatures (93° C. versus 45° C.) through the incorporation of 10% acetone in the desorbent water.
Figure 7B:
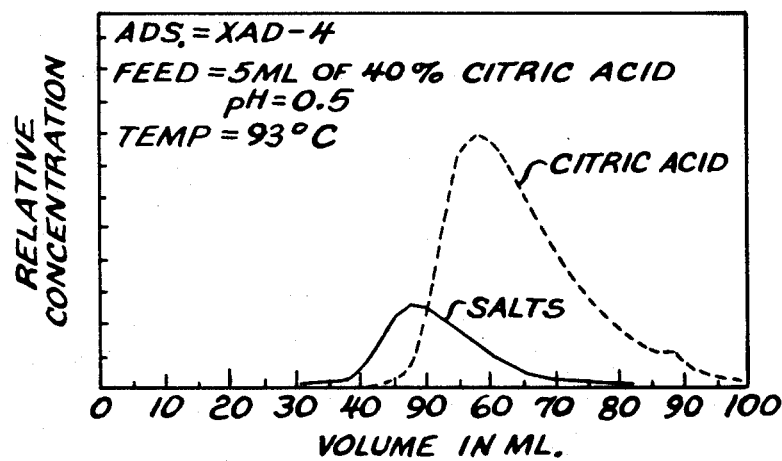
Figure 7C:
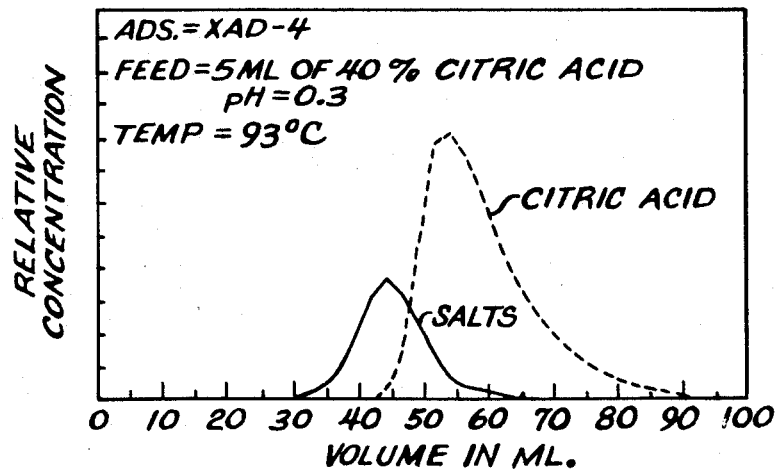

The separation example represented by FIGS. 7B and 7C required high temperatures, e.g., 93° C. to achieve the separation of 40% citric acid due to the difficulty in desorbing citric acid from the XAD-4 adsorbent. In this example, high temperatures, which adversely affect the adsorbent life and the cost to operate, are eliminated and the separation is readily achieved at 45° C. through the use of a desorbent mixture of 10% (by wt.) acetone and 90% water. Referring to FIG. 9, a feed comprising 40% (wt.) citric acid, 4% carbohydrates and 2% salts of the following elements: $K^+$, $Na^+$, $Mg^{++}$, $Fe^{+++}$, $Ca^{++}$ plus proteins and amino acids, was introduced into the pulse test apparatus as set forth previously and the test ran as before except that the temperature was 45° C. In this test, the pH was maintained at 0.5, but the desorbent contained acetone as mentioned above. The net retention volume for citric acid was 10.7 ml, and the resolution was 0.61 and, therefore, the separation was easily made.

What is claimed is:

1. A process for separating citric acid from a fermentation broth feed mixture comprising contacting said mixture with a neutral polymeric adsorbent selected from the group consisting of an insoluble, crosslinked, polystyrene polymer and a nonionic, hydrophobic, insoluble polyacrylic ester polymer at adsorption conditions selected to selectively adsorb said citric acid.

2. The process of claim 1 further characterized in that said citric acid is recovered by desorption with a desorbent at desorption conditions.

3. The process of claim 2 further characterized in that said adsorption and desorption conditions include a temperature within the range of from about 20° C. to about 200° C. and a pressure within the range of from about atmospheric to about 500 psig (3450 kPa gauge).

4. The process of claim 3 further characterized in that said adsorption is effected in the liquid phase with water.

5. The process of claim 1 further characterized in that the pH of said feed mixture is lower than the first ionization constant ($kPa_1$) of citric acid.

6. The process of claim 1 further characterized in that said adsorbent is a neutral styrene-divinylbenzene crosslinked polymer.

7. The process of claim 1 further characterized in that said adsorbent is a neutral polyacrylic ester resin.

8. The process of claim 7 further characterized in that said adsorbent has a surface area of at least 10 $m^2/g$.

9. The process of claim 1 wherein said desorbent is water.

10. The process of claim 1 wherein said desorbent is a mixture of water and acetone.

11. The process of claim 10 wherein said desorbent contains up to 15% acetone.

12. The process of claim 11 wherein said desorbent contains from 5-10% acetone.

13. The process of claim 1 wherein said fermentation broth comprises citric acid, carbohydrates and salts.

14. A process for separating citric acid from a feed mixture comprising a fermentation broth, which process employs an adsorbent selected from the group consisting of a nonionic, hydrophobic, insoluble crosslinked polystyrene polymer and a nonionic, hydrophobic, insoluble crosslinked polyacrylic ester polymer which process comprises the steps of:

(a) maintaining net fluid flow through a column of said adsorbent in a single direction, which column contains at least three zones having separate operational functions occurring therein and being serially interconnected with the terminal zones of said column connected to provide a continuous connection of said zones;

(b) maintaining an adsorption zone in said column, said zone defined by the adsorbent located between a feed input stream at an upstream boundary of said zone and a raffinate output stream at a downstream boundary of said zone;

(c) maintaining a purification zone immediately upstream from said adsorption zone, said purification zone defined by the adsorbent located between an extract output stream at an upstream boundary of said purification zone and said feed input stream at a downstream boundary of said purification zone;

(d) maintaining a desorption zone immediately upstream from said purification zone, said desorption zone defined by the adsorbent located between a desorbent input stream at an upstream boundary of said zone and said extract output stream at a downstream boundary of said zone;

(e) passing said feed mixture into said adsorption zone at adsorption conditions to effect the selective adsorption of said citric acid by said adsorbent in said adsorption zone and withdrawing a raffinate output stream comprising the nonadsorbed components of said fermentation broth from said adsorption zone;

(f) passing a desorbent material into said desorption zone at desorption conditions to effect the displacement of said citric acid from the adsorbent in said desorption zone;

(g) withdrawing an extract output stream comprising said citric acid and desorbent material from said desorption zone;

(h) passing at least a portion of said extract output stream to a separation means and therein separating at separation conditions at least a portion of said desorbent material; and, (i) periodically advancing through said column of adsorbent in a downstream direction with respect to fluid flow in said adsorption zone the feed input stream, raffinate output stream, desorbent input stream, and extract output stream to effect the shifting of zones through said adsorbent and the production of extract output and raffinate output streams.

15. The process of claim 14 further characterized in that it includes the step of passing at least a portion of said raffinate output stream to a separation means and therein separating at separation conditions at least a portion of said desorbent material to produce a raffinate product having a reduced concentration of desorbent material.

16. The process of claim 14 further characterized in that it includes the step of maintaining a buffer zone immediately upstream from said desorption zone, said buffer zone defined as the adsorbent located between the desorbent input stream at a downstream boundary of said buffer zone and the raffinate output stream at an upstream boundary of said buffer zone.

17. The process of claim 14 further characterized in that said adsorption conditions and desorption conditions include a temperature within the range of from about 20° C. to about 200° C. and a pressure within the range of from about atmospheric to about 500 psig (3450 kPa gauge) to ensure liquid phase.

18. The process of claim 14 further characterized in that said desorbent comprises water.

19. The process of claim 14 wherein said desorbent is a mixture of water and acetone.

20. The process of claim 14 further characterized in that the pH of said feed mixture is lower than the first ionization constant ($pKa_1$) of citric acid.

21. The process of claim 14 wherein the pH of the said feed mixture is below 3.13.

22. The process of claim 14 wherein said fermentation broth comprises citric acid, carbohydrates and salts.

23. The process of claim 22 wherein said fermentation broth additionally contains proteins and amino acids.

* * * * *